(12) United States Patent
Bunt

(10) Patent No.: US 12,090,150 B2
(45) Date of Patent: Sep. 17, 2024

(54) DEUTERATED ANALOGS OF ELACRIDAR

(71) Applicant: Izumi Technology, LLC, Lexington, MA (US)

(72) Inventor: Antonius Bunt, Lexington, MA (US)

(73) Assignee: Izumi Technology, LLC, Lexignton, MA (US)

( * ) Notice: Subject to any disclaimer, the term of this patent is extended or adjusted under 35 U.S.C. 154(b) by 0 days.

(21) Appl. No.: 17/990,722

(22) Filed: Nov. 20, 2022

(65) Prior Publication Data

US 2023/0158013 A1 May 25, 2023

Related U.S. Application Data

(63) Continuation of application No. 17/027,359, filed on Sep. 21, 2020, now Pat. No. 11,504,366, which is a continuation-in-part of application No. PCT/US2019/023443, filed on Mar. 21, 2019.

(60) Provisional application No. 62/646,238, filed on Mar. 21, 2018.

(51) Int. Cl.
*A61K 31/473* (2006.01)
*A61K 45/06* (2006.01)
*C07D 401/12* (2006.01)

(52) U.S. Cl.
CPC ............ *A61K 31/473* (2013.01); *A61K 45/06* (2013.01); *C07D 401/12* (2013.01)

(58) Field of Classification Search
None
See application file for complete search history.

(56) References Cited

FOREIGN PATENT DOCUMENTS

WO        WO 98/52923        * 11/1998        ........... C07D 219/06

OTHER PUBLICATIONS

Giacone et al., Journal of Pharmaceutical Sciences (2018), 107, pp. 698-705 (available online Sep. 19, 2017).*

* cited by examiner

*Primary Examiner* — Brian J Davis
(74) *Attorney, Agent, or Firm* — The Fedde Law Firm; Kenton Fedde; Nathaniel Fedde

(57) ABSTRACT

The present invention relates to efflux inhibitor compounds, compositions, and methods of using the same. More specifically, the instant invention comprises deuterated analogs of elacridar with superior pharmacokinetic properties such that it is now possible to facilitate accumulation and distribution of therapeutic agents to effective levels in cells or compartments protected by efflux transporter proteins such as Breast Cancer Resistance Protein (BCRP) and P-Glycoprotein (P-GP). Such transporter protected compartments include brain, spinal cord, nerves, cerebrospinal fluid, testis, eyeballs, retina, inner ear, placenta, mammary gland, liver, biliary tract, kidney, intestines, lung, adrenal cortex, endometrium, hematopoietic cells, stem cells, and solid tumors. In other embodiments, the present invention comprises methods of using the instant deuterated analogs.

20 Claims, 10 Drawing Sheets

9,10-dihydro-5-methoxy-9-oxo-N-{4-[2-{1´,2,3,4-tetrahydro- 6,7-dimethoxy-2-isoquinolinyl}ethyl] phenyl}-4-acridine-carboxamide

| Fig. 2A | Fig. 2B |
|---|---|
| Fig. 2C | Fig. 2D |

Compound 1

6-Amino-5-methoxy-cyclohexa-1,3-dienecarboxylic acid

Compound 2

2-Bromo-benzoic acid

Compound 5

1-(2-Bromo-ethyl)-4-nitro-benzene

Compound 6

6-Amino-5-methoxy-cyclohexa-1,3-dienecarboxylic acid

DEUTERATED ANALOGS OF ELACRIDAR

RELATED APPLICATIONS

This application claims priority to PCTUS1923443, filed 2019-Mar. 21, which claims benefit of U.S. Provisional Application Ser. No: 62646238, filed 2018-Mar. 21.

TECHNICAL FIELD

The present invention relates to deuterated active pharmaceutical ingredients and to efflux inhibitors.

BACKGROUND

Elacridar, previously referred to as GF120918, is a compound with the structure of 9,10-dihydro-5-methoxy-9-oxo-N-[4-[2-(1,2,3,4-tetrahydro-6,7-dimethoxy-2-isoquinolinyl)ethyl]phenyl]-4-acridine-carboxamide or, as sometimes written, N-4-[2-(1,2,3,4-tetrahydro-6,7-dimethoxy-2-isoquinolinyl)ethyl]-phenyl)-9,10-dihydro-5-methoxy-9-oxo-4-acridine carboxamide. Elacridar was originally described as a P-gp selective inhibitor but is now recognized as a dual P-gp/BCRP inhibitor. (Matsson P, Pedersen J M, Norinder U, Bergström C A, and Artursson P 2009 Identification of novel specific and general inhibitors of the three major human ATP-binding cassette transporters P-gp, BCRP and MRP2 among registered drugs. Pharm Res 26:1816-1831).

Elacridar has been examined with some success both in vitro and in vivo as a P-gp and BCRP inhibitor. By way of example, in cancer patients, coadministration of elacridar with therapeutic agents such as paclitaxel (P-gp substrate) and topotecan (BCRP substrate) improved their oral absorption—presumably by preventing efflux into the intestinal lumen by P-gp/BCRP pumps located in the GI tract. Similarly, in rodents, elacridar has been coadministered with some success with pump substrates such as morphine, amprenavir, imatinib, dasatinib, gefitinib, sorafenib, and sunitinib to increase drug levels in the brain (by blocking efflux mediated by P-gp and BCRP at the blood brain barrier). A summary of some of these studies can be found in a study report by Sane et al. (Drug Metabolism And Disposition 40:1612-1619, 2012).

Administration of elacridar has several limitations. By way of example, elacridar has unfavorable physicochemical properties; it is practically insoluble in water, making it difficult to formulate as, for example, either an injectable or oral dosage form. Elacridar's poor solubility and high lipophilicity result in dissolution rate-limited absorption from the gut lumen.

A variety of approaches have been pursued in order to increase efficacy of elacridar. For example, United States Patent Application Publication 20140235631 discloses a nanoparticle formulation in order to increase oral bioavailability.

Sane et al. (Journal of Pharmaceutical Sciences, Vol, 102, 1343-1354 (2013)) report a micro-emulsion formulation of elacridar to try and overcome its dissolution-rate-limited bioavailability.

Sawicki et al. (Drug Development and Industrial Pharmacy, 2017 VOL. 43, NO. 4, 584-594) described an amorphous solid dispersion formulation of freeze dried elacridar hydrochloride—povidone K30-sodium dodecyl sulfate. However, when tested in healthy human volunteers, extremely high doses (e.g. 1000 mg) were required to achieve a Cmax of 326 ng/ml. (Sawicki et al. Drug Deliv. and Transl. Res. Published online 18 Nov. 2016).

Montesinos et al. (Mol Pharm. 2015 Nov. 2; 12(11):3829-38) attempted several PEGylated liposome formulations of elacridar which resulted in a partial increase in half life, but without an increase in efficacy when co-administered with a therapeutic agent.

Because of the great unpredictability in the art and poor correlations in many cases between animal and human data, the value of such formulation attempts await clinical trial.

Studies of the whole body distribution of a microdose of $^{11}C$ elacridar after intravenous injection showed high level accumulation in the liver (Bauer et al. J Nucl Med. 2016; 57:1265-1268). This has led some to suggest that systemic levels of elacridar are also substantially limited by clearance in the liver.

A potentially attractive strategy for improving metabolic stability of some drugs is deuterium modification. In this approach, one attempts to slow the CYP-mediated metabolism of a drug or to reduce the rate of formation of inactive metabolites by replacing one or more hydrogen atoms with deuterium atoms. Deuterium is a safe, stable, non-radioactive isotope of hydrogen. Compared to hydrogen, deuterium forms stronger bonds with carbon. In select cases, the increased bond strength imparted by deuterium can positively impact the absorption, distribution, metabolism, excretion and/or toxicity ('ADMET') properties of a drug, creating the potential for improved drug efficacy, safety, and/or tolerability. At the same time, because the size and shape of deuterium are essentially identical to those of hydrogen, replacement of hydrogen by deuterium would not be expected to affect the biochemical potency and selectivity of the drug as compared to the original chemical entity that contains only hydrogen.

Over the past 35 years, the effects of deuterium substitution on the rate of metabolism have been reported for a very small percentage of approved drugs (see, e.g., Blake, M I et al, J Pham Sci, 1975, 64:367-91; Foster, A B, Adv Drug Res 1985, 14:1-40 ("Foster"); Kushner, D J et al, Can J Physiol Pharmacol 1999, 79-88; Fisher, M B et al, Curr Opin Drug Discov Devel, 2006, 9:101-09 ("Fisher")), The results have been variable and unpredictable. For some compounds, deuteration indeed caused decreased metabolic clearance in vivo. For others, no change in metabolism was observed. Still others demonstrated increased metabolic clearance. The great unpredictability and variability in deuterium effects has led experts to question or dismiss deuterium modification as a viable drug design strategy for inhibiting metabolism (see Foster at p. 35 and Fisher at p. 101).

The effects of deuterium modification on a drug's metabolic properties are not predictable even when deuterium atoms are incorporated at known sites of metabolism. Only by actually preparing and testing a deuterated drug can one determine if and how the rate of metabolism will differ from that of its non-deuterated counterpart. See, for example, Fukuto et al. (J. Med. Chem, 1991, 34, 2871-76). Many drugs have multiple sites where metabolism is possible. The site(s) where deuterium substitution is required and the extent of deuteration necessary to see an effect on metabolism, if any, will be different for each drug.

Considering elacridar's challenging physicochemical and ADMET properties in humans, in spite of recent formulation advancements, there remains a need in the art for elacridar analogs that can achieve higher, less variable levels in the systemic circulation, at the blood-brain barrier, and elsewhere to optimize efflux inhibition.

SUMMARY OF THE INVENTION

This present invention provides deuterated analogs of elacridar. In one embodiment, a deuterated analog of the invention comprises elacridar comprising one or two or three or four or five or six or seven or eight or nine or ten or 11 or 12 or 13 or 14 or 15 or 16 or 17 or 18 or 19 or 20 or more deuterium atoms substituted for hydrogen atoms, wherein, collectively, the substitutions are located at one or more of locants 2-4, 7-19, 23-39, and 41-43 as designated in FIG. 1. In other embodiments, instant analogs comprise 1-4 deuterium substitutions, wherein, collectively, the substitutions are located at one or more of locants 5 and 6 in addition to one or more deuterium substitutions at one or more of locants of locants 2-4, 7-19, 23-39, and 41-43. The instant invention also includes compositions comprising the instant analogs and methods of using the same.

The various instant deuterated analogs of elacridar are represented by formula 1:

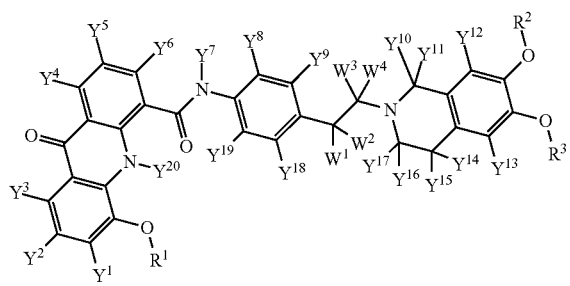

or a pharmaceutically acceptable salt thereof, comprising at least one deuterium atom wherein:
each Y and each W are independently selected from hydrogen or deuterium; and
each R is independently selected from CH3, CH2D1, CH1D2, and CD3 with the proviso that when each Y is H and when each R is CH$_3$, then at least one W is H. For the convenience of the reader, this proviso is referred to herein as Proviso A.

BRIEF DESCRIPTION OF THE FIGURES

FIG. 2 is subdivided into four sheets labeled FIGS. 2A-2D.
FIG. 7 is a smaller scale view of FIG. 7 showing the whole formed by the partial views of FIG. 2 and indicating the positions of the features shown.

DETAILED DESCRIPTION OF THE INVENTION

Figure 1:
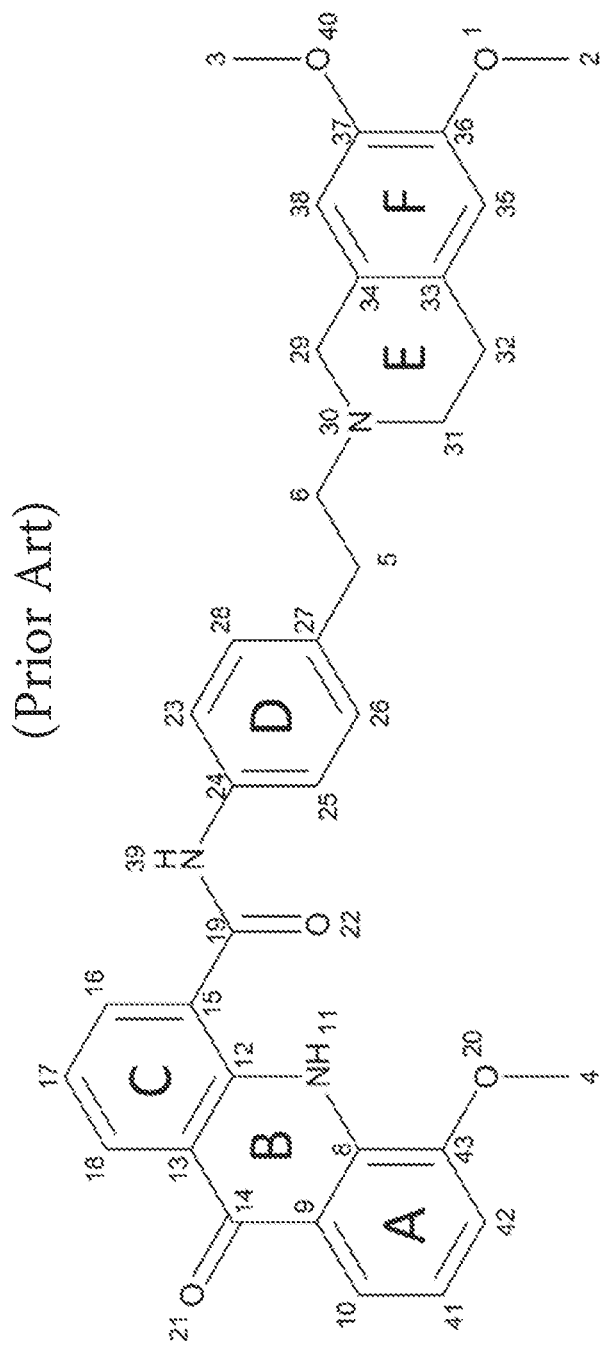
FIG. 1 shows elacridar with locant numbers.

As used here, the following definitions and abbreviations apply.
"AUC" or "AUC 0-$_\infty$" is the area under the curve from time 0 extrapolated to infinite time.

"Co-administered" (or "co-therapy" or "in combination with") in reference to instant analogs or compositions with therapeutic agent(s), is meant to include the administration of such analogs or composition in a single dosage form, in separate dosage forms at the same time, or in separate dosage forms and different times. Optionally, co-administration can be provided in any manner that results in a second therapeutic agent being present in a subject at the same time as the elacridar analog.

"DMF" means N,N-Dimethylformamide
"Deuterium atoms substituted" or "deuterium atoms are substituted", as used herein, refers to a deuterium atom that is substituted for a hydrogen atoms.

"Elacridar" means 9,10-dihydro-5-methoxy-9-oxo-N-[4-[2-(1,2,3,4-tetrahydro-6,7-dimethoxy-2-isoquinolinyl)ethyl] phenyl]-4-acridine-carboxamide or N-(4-(2-(1,2,3,4-tetrahydro-6,7-dimethoxy-2-isoquinolinyl)ethyl)phenyl)-9,10-dihydro-5-methoxy-9-oxo-4-acridine carboxamide. The term "elacridar" is also meant to embrace the compound of the same structure described above, excepting for one or more hydrogens being replaced by a deuterium; such a compound is also referred to as a deuterated analog of elacridar or an elacridar analog. Unless otherwise clear by the context, the term "elacridar" means an unsubstituted elacridar.

"Elacridar analog(s)" or "instant analog" means an elacridar analog of the instant invention.

"Isotopologue", as used herein, refers to a species in which the chemical structure differs from a specific compound of this invention only in the isotopic composition thereof.

"Isotopic enrichment factor", as used herein, means the ratio of the isotopic abundance in an instant analog and the natural abundance of a specified isotope (e.g. deuterium).

"Isotopic purity", as used herein, is the percentage of analogs molecules in a composition that contain the designated number of deuterated atoms at the designated deuteration sites.

"Kp, brain", as used here, is the brain-to-plasma partition coefficient as measured, e.g., as set forth in Sane et al, Drug Metabolism And Disposition vol. 40 no. 8 1612-1619.

"Normal valence", when used in reference to the instant analogs, refers to the combining power of an element as measured by the number of hydrogen plus deuterium atoms it can displace or combine with. For the sake of clarity, the normal valence of carbon is 4, of oxygen is 2, and of nitrogen is 3.

"Pharmaceutically acceptable," as used herein, refers to a component that is, within the scope of sound medical judgment, suitable for use in contact with the tissues of humans and other mammals, optionally without undue toxicity, irritation, or immunogenicity and are commensurate with a reasonable benefit/risk ratio.

"Pharmaceutically acceptable salt" means any non-toxic salt that, upon administration to a recipient, is capable of providing, either directly or indirectly, an analog of the instant invention.

"TBTU" means 241 H-Benzotriazole-1-yl)-1,1,3,3-tetramethylaminium tetrafluoroborate.

"Unsubstituted elacridar" means elacridar where each atom has a natural isotopic abundance.

Through insight in the mind of the inventor, it has now been discovered that achieving therapeutic levels of elacridar in the systemic circulation is greatly inhibited by pre-systemic clearance (also known as first pass metabolism) in the gastro-intestinal (GI) tract and the liver and pre and post-systemic biotransformation (or elimination). Such biotransformation, according to insight by the inventor, results in inactive metabolites through specific enzymatic modification, e.g. by cytochrome monogenases and oxidoreductases in the GI tract and liver. Accordingly, certain deuterated elacridar analogs have been designed to block metabolic degradation and substantially increase systemic and CNS levels following oral or intravenous or other routes of administration. It has also been discovered, according to the mind of the inventor, that certain elacridar metabolites can be responsible for toxicity. Accordingly, the elacridar analogs of the present invention should be safer and demonstrate fewer toxicities.

Elacridar Analog Nomenclature

For convenience of the reader, elacridar and elacridar analogs are named in reference to the structure shown in FIG. 1. Each potential deuteration site is assigned a locant number. Each ring is assigned a letter. There are two linkers, namely a carboximide linker between ring C and ring D (linker 1) and an ethyl linker between ring D and ring E. For additional clarity, constituents of a ring which are not part of a linker are deemed to be part of the ring.

Specific Embodiments

By example, the invention contemplates each of the exemplary embodiments ("EE") listed below. Each of the EEs is an instant analog according to the invention. It should be understand that where a locant is not specified, it can be a hydrogen or a deuterium.

EE1. With Proviso A, an analog comprising elacridar having one or more deuterium atoms substituted (i.e. one or more hydrogen atoms are substituted with respective deuterium atoms). Such substitutions can be provided, wherein the normal valence of each atom is maintained.

EE2. The analog of EE1 wherein 1, 2, 3, 4, 5, 6, 7, or 8 deuterium atoms are substituted in ring E.

EE3. The analog of EE1 or EE2 wherein 1, 2, 3, 4, 5, 6 7, 8, 9, 10, 11, or 12 deuterium atoms are substituted in ring F.

EE3.1 The analog of any of EE1-EE3 wherein 1, 2, or 3 deuterium atoms are substituted in ring A.

EE3.2 The analog of any of EE1-EE3.1 wherein 1, 2, or 3 deuterium atoms are substituted in ring C.

EE3.3 The analog of any of EE1-EE3.2 wherein 1, 2, 3, or 4 deuterium atoms are substituted in ring D.

EE3.3 The analog of any of EE1-EE3.3 wherein 1, 2, or 3 deuterium atoms are substituted at locant 4.

EE4. The analog of any of EE1-EE3.3 wherein 1 or 2 deuterium atoms are substituted at locant 32.

EE5. The analog of any of EE1-EE44 wherein 2 deuterium atoms are substituted at locant 32.

EE6. The analog of any of EE1-EE5 wherein one or two deuterium atoms are substituted at locant 31.

EE7. The analog of any of EE1-EE5 wherein two deuterium atoms are substituted at locant 31.

EE8. The analog of any of EE1-EE7 wherein one or two deuterium atoms are substituted at locant 29.

EE9. The analog of any of EE1-EE7 wherein two deuterium atoms are substituted at locant 29.

EE10. The analog of any of EE1-EE9 wherein one or two deuterium atoms are substituted at locant 5.

EE11. The analog of any of EE1-EE9 wherein two deuterium atoms are substituted at locant 5.

EE12. The analog of any of EE1-EE11 wherein one or two deuterium atoms are substituted at locant 6.

EE13. The analog of any of EE1-EE11 wherein two deuterium atoms are substituted at locant 6.

EE14. The analog of any of EE1-EE11 wherein one or two or three deuterium atoms are substituted at locant 2.

EE15. The analog of any of EE1-EE11 wherein three deuterium atoms are substituted at locant 2.

EE16. The analog of any of EE1-EE15 wherein one or two or three deuterium atoms are substituted at locant 3.

EE17. The analog of any of EE1-EE15 wherein three deuterium atoms are substituted at locant 3.

EE18. The analog of EE1 wherein two deuterium atoms are substituted at each of locant 5, 6, 29, 31, and 32 and three deuterium atoms are substituted at each of locant 2 and 3.

EE19. The analog of any of the previous EEs, wherein at said locant(s) that contain substitutions, all hydrogen atoms at said locant(s) are substituted by respective deuterium atoms.

EE20. The analog of EE1 wherein one, two, or three deuterium atoms are substituted at locant 2 and one, two, or three deuterium atoms are substituted at locant 3.

EE21, The analog of EE1 wherein three deuterium atoms are substituted at locant 2 and three deuterium atoms are substituted at locant 3.

EE22. The analog of any of EE1 and EE20-EE21 wherein one, two, or three deuterium atoms are substituted at locant 4.

EE23. The analog of any of EE1 and EE20-EE21 wherein three deuterium atoms are substituted at locant 4.

EE24. The analog of any of EE1 and EE20-EE23 wherein one deuterium atom is substituted at at least one of locants 23, 25, 26, and 28 (i.e. one or more of locants 23, 25, 26, and 28 can contain a deuterium substitution).

EE25. The analog of any of EE1 and EE20-EE23 wherein one deuterium atom is substituted at each of locants 23 and 25.

EE26. The analog of any of EE1 and EE20-EE23 wherein one deuterium atom is substituted at each of locants 26 and 28.

EE27. The analog of any of EE1 and EE20-EE23 wherein one deuterium atom is substituted at each of locants 23, 25, 26, and 28.

EE28. The analog of any of EE1 and EE20-EE27 a Therein one or two deuterium atoms are substituted at locant 32.

EE29. The analog of any of EE1 and EE20-EE27 wherein two deuterium atoms are substituted at locant 32.

EE30. The analog of any of EE1 and EE20-EE29 wherein one or two deuterium atoms are substituted at locants 31 or 29 or 31 and 29.

EE31. The analog of any of EE1 and EE20-EE29 wherein two deuterium atoms are substituted at each of locants 31 and 29.

EE32. The analog of any of EE1 and EE20-EE31 wherein one deuterium atom is substituted at one or more of locants 10, 41, 42, 16, 17, and 18.

EE33. The analog of EE1 wherein one to 31 deuterium atoms are substituted at a carbon atom.

EE34. The analog of EE1 wherein or more or all of the carbon atoms at locants 2, 3, 5, 6, 10, 16, 17, 18. 23, 25, 26, 28, 29, 31, 32, 41, and 42 are deuterated EE35, The analog of EE1 or EE33 comprising at least one of:
i. one deuterium atom substituted at one or more of locants 10, 41, and 42;
ii. one deuterium atoms substituted at one or more of locants 16, 17, and 18;

iii. one deuterium atoms substituted at one or more of locants 23, 25, 26, and 28;
iv. one or two deuterium atoms substituted at one or more of locants 29, 31, and 32;
v. one or two deuterium atoms substituted at one or more of locants 5 and 6; and
vi. one or two or three deuterium atoms substituted at one or more of locants 2 and 3.

EE36. The analog of EE1 or EE33 comprising at least two of:
i. one deuterium atom substituted at one or more of locants 10, 41, and 42;
ii. one deuterium atoms substituted at one or more of locants 16, 17, and 18;
iii one deuterium atoms substituted at one or more of locants 23, 25, 26, and 28;
iv. one or two deuterium atoms substituted at one or more of locants 29, 31, and 32;
v. one or two deuterium atoms substituted at one or more of locants 5 and 6; and
vi. one or two or three deuterium atoms substituted at one or more of locants 2 and 3.

EE37. The analog of EE1 or EE33 comprising at least three of:
i. one deuterium atom substituted at one or more of locants 10, 41, and 42;
ii. one deuterium atoms substituted at one or more of locants 16, 17, and 18
iii. one deuterium atoms substituted at one or more of locants 23, 25, 26, and 28
iv. one or two deuterium atoms substituted at one or more of locants 29, 31, and 32;
v. one or two deuterium atoms substituted at one or more of locants 5 and 6; and
vi. one or two or three deuterium atoms substituted at one or more of locants 2 and 3.

EE38. The analog of EE1 or EE33 comprising at least four of:
i. one deuterium atom substituted at one or more of locants 10, 41, and 42;
ii. one deuterium atom substituted at one or more of locants 16, 17, and 18
iii. one deuterium atoms substituted at one or more of locants 23, 25, 26, and 28.
iv. one or two deuterium atoms substituted at one or more of locants 29, 31, and 32;
v. one or two deuterium atoms substituted at one or more of locants 5 and 6; and
vi. one or two or three deuterium atoms substituted at one or more of locants 2 and 3.

EE39. The analog of EE1 or EE33 comprising:
i. one deuterium atom substituted at one or more of locants 10, 41, and 42;
ii. one deuterium atom substituted at one or more of locants 16, 17, and 18;
iii. one deuterium atoms substituted at one or more of locants 23, 25, 26, and 28;
iv. one or two deuterium atoms substituted at one or more of locants 29, 31, and 32;
v. one or two deuterium atoms ubstituted at one or more of locants 5 and 6; and
vi. one or two or three deuterium atoms substituted at one or more of locants 2 and 3.

EE40. The analog of EE1 or EE33 comprising:
i. one deuterium atom substituted at two or more of locants 10, 41, and 42 (i.e. two of these locants each contain one substitution);
ii. one deuterium atom substituted at two or more of locants 16, 17, and 18;
iii. one deuterium atoms substituted at two or more of locants 23, 25, 26, and 28;
iv. one or two deuterium atoms substituted at one or more of locants 29, 31, and 32;
v. one or two deuterium atoms substituted at one or more of locants 5 and 6; and
vi. one or two or three deuterium atoms substituted at each of locants 2 and 3.

EE41. The analog of EE1 or EE33 comprising:
i. one deuterium atom substituted at each of locants 10, 41, and 42;
ii. one deuterium atom substituted at each of locants 16, 17, and 18;
iii. one deuterium atoms substituted at three or more of locants 23, 25, 26, and 28;
iv. one or two deuterium atoms substituted at two or more of locants 29, 31, 32;
v. one or two deuterium atoms substituted at each of locants 5, and 6; and
vi. one or two or three deuterium atoms substituted at each of locants 2 and 3.

EE42. The analog of EE1 or EE33 comprising:
i. one deuterium atom substituted at each of locants 10, 41, and 42;
ii. one deuterium atom substituted at each of locants 16, 17, and 18;
iii. one deuterium atoms substituted at each of locants 23, 25, 26, and 28;
iv. one or two deuterium atoms substituted at each of locants 29, 31, 32;
v. one or two deuterium atoms substituted at each of locants 5 and 6; and
vi. one or two or three deuterium atoms substituted at each of locants 2 and 3.

EE45. The analog of EE1 or EE33 comprising:
i. one deuterium atom substituted at each of locants 10, 41, and 42;
ii one deuterium atom substituted at each of locants 16, 17, and 18;
iii. one deuterium atoms substituted at each of locants 23, 25, 26, and 28;
iv. two deuterium atoms substituted at each of locants 29, 31, 32,
v. two deuterium atoms substituted at each of locants 5 and 6; and
vi. two or three deuterium atoms substituted at each of locants 2 and 3.

EE46. The analog of EE1 or EE33 comprising:
i. one deuterium atom substituted at each of locants 10, 41, and 42;
ii. one deuterium atom substituted at each of locants 16, 17, and 18;
iii. two deuterium atoms substituted at each of locants 29, 31, 32,
iv. two deuterium atoms substituted at each of locants 5 and 6; and
v. three deuterium atoms substituted at each of locants 2 and 3.

EE47. The analog of any of EE1 EE46 comprising one or two or three deuterium atoms substituted at locant 4.

EE48. The analog of Formula 1 comprising at least one deuterium atom, wherein Each Y and each W is independently selected from hydrogen or deuterium: and each R is independently selected from $CH_3$, $CH_2D_1$, $CH_1D_2$, and $CD_3$ with Proviso A.

Applicants have conducted a series of in vivo and in vitro experiments to elucidate the metabolism of elacridar by the liver and possibly elsewhere. Other studies were conducted to investigate the effect of deuteration at various sites on such metabolism. These results, combined with rational design have allowed the Applicant, through creative insight in the mind of the Applicant, to devise the following subgenera to be remarkably stable compared to the unsubstituted parent. Moreover, in the mind of the inventor, these analogs block formation of metabolites which are in part, responsible for toxicity of the unsubstituted parent.

EE49. The analog of EE48 wherein Y14 and Y15 each consist of deuterium and optionally wherein each of the remaining Ys, Ws, and Rs do not comprise a deuterium.

EE50. The analog of EE48 wherein W3 and W4 each consist of deuterium and optionally wherein each of the remaining Ys. Ws, and Rs do not comprise a deuterium.

EE51. The analog of EE48 wherein W1-W4 each consist of deuterium and optionally wherein each of the remaining Ys, Ws, and Rs do not comprise a deuterium.

EE52. The analog of any one of EE48-EE51 wherein R2 and R3 each consist of $CD_3$ and optionally wherein each of the remaining Ys, Ws, and Rs do not comprise a deuterium.

EE53. The analog of any one of EE48-EE51 wherein R2 and R3 each consist of $CD_3$ and wherein Y14 and Y15 each consist of deuterium and optionally wherein each of the remaining Ys, Ws, and Rs do not comprise a deuterium.

EE54. The analog of any one of EE48-EE51 wherein Y2 is deuterium and optionally wherein each of the remaining Ys, Ws, and Rs do not comprise a deuterium.

EE55. The analog of any one of EE48-EE51 wherein Y2 is deuterium and R2 and R3 each consist of $CD_3$ and optionally wherein each of the remaining Ys, Ws, and Rs do not comprise a deuterium.

EE56. The analog of any one of EE48-EE51 wherein R1 is $CD_3$ and optionally wherein each of the remaining Ys. Ws, and Rs do not comprise a deuterium.

EE57. The analog of any one of EE48-EE51 wherein Y9 and Y18 each consist of deuterium and optionally wherein each of the remaining Ys, Ws, and Rs do not comprise a deuterium.

EE58. The analog of any one of EE48-EE51 wherein Y2, Y9, Y18, and W1-W4 each consist of deuterium and R1-R3 each consist of CD, and optionally wherein each of the remaining Ys, Ws, and Rs do not comprise a deuterium.

EE59. The analog of EE48 wherein R1, R2 and R3 each consist of $CD_3$ and W14 and Y15 each consist of deuterium and wherein each of the remaining Ys, Ws, and Rs do not comprise a deuterium.

EE60. The analog of EE48 wherein wherein each Y except Y7 and Y20 consist of $CD_3$. and each W consist of deuterium and R1-R3 each consist of $CD_3$.

EE61. The analog of any of the preceding EE analogs wherein the analog is present in an isotopic purity of greater than 50%.

EE62. The analog of any of the preceding EE analogs wherein the analog is present in an isotopic purity of greater than 70%.

EE63. The analog of any of the preceding EE analogs wherein the analog is present in an isotopic purity of greater than 90%.

EE64. The analog of any of the preceding EE analogs wherein there is at least a 20% increase in one or more of in vivo plasma half life in humans, in vitro half life, AUC 0-∞", and Cmax when compared to unsubstituted elacridar.

EE65. The analog of any of the preceding EE analogs wherein there is at least a 40% increase in one or more of in vivo plasma half life in humans, in vitro half life, AUC 0-¢", and Cmax when compared to unsubstituted elacridar.

EE66. The analog of any of the preceding EE analogs wherein there is at least a 40% increase in one or more of in vivo plasma half life when administered in humans, in vitro half life, AUC 0-∞", and Cmax when compared to unsubstituted elacridar.

EE67. The analog of any of the preceding EE analogs wherein there is at least a 60% increase in one or more of in vivo plasma half life in humans, in vitro half life, AUC 0-∞", and Cmax when compared to unsubstituted elacridar.

EE68. The analog of any of the preceding EE analogs wherein there is at least a 100% increase in one or more of in vivo plasma half life in humans, in vitro half life, AUC 0-∞", and Cmax when compared to unsubstituted elacridar.

EE69. A composition comprising the analog of any of the preceding EE analogs further comprising a therapeutic agent.

EE70. A composition of EE69 wherein the therapeutic agent is selected from the group consisting of paclitaxel, topotecan, dasatinib, gefitinib, imatinib, pazopanib, sorafenib, sunitinib, vandetanib, erlotinib, crizotinib, docetaxel, doxorubicin, imidazotetrazine, ispinesib, paclitaxel, tazemetostat, temozolomide, topotecan, vinca alkaloid, anthracyclines, taxol, taxol derivatives, podophyllotoxins, mitoxantrone, actinomycin, colchicine, gramicidine D, amsacrine, abacavir, amprenavir, lamivudine, ritonavir, zidovudine, loperamide, morphine, n-desmethylloperamide, and pazopanib.

EE71. The analog of any one of EE1-EE68 wherein when administered orally in at least one of a human, a rat, or a mouse at a dosage level of at least one of 1 mg/kg, 5 mg/kg, or 10 mg/kg, and coadministered orally with a therapeutic agent of EE78 at 20 mg/kg, said administration results in an increase in Kp, brain of the therapeutic agent of at least 20%.

EE72. The analog of any one of EE1-EE68 wherein when administered orally in at least one of a human, a rat, or a mouse at a dosage level of at least one of 1 mg/kg, 5 mg/kg, or 10 mg/kg, and coadministered orally with erlotinib at 20 mg/kg, said administration results in an increase in Kp, brain of erlotinib of at least 20%.

EE80-EE106. These analogs are shown in Tables 1-3. The locants refer to Formula 1. Where a W or Y locant is blank, the locant it can be a H or D. Where an R locant is blank, it can be a CH3, CH2D1, CH1 D2, or CD3. "Digin" represents the minimum number of deuterium atoms per molecule.

TABLE 1

| | EE80 | EE81 | EE82 | EE83 | EE84 | EE85 | EE86 | EE87 | EE88 | EE89 |
|---|---|---|---|---|---|---|---|---|---|---|
| Y1 | | | | | | | | | | |
| Y2 | | | | | | D | D | | | D |
| Y3 | | | | | | | | | | |
| Y4 | | | | | | | | | | |
| Y5 | | | | | | | | | | |

TABLE 1-continued

|  | EE80 | EE81 | EE82 | EE83 | EE84 | EE85 | EE86 | EE87 | EE88 | EE89 |
|---|---|---|---|---|---|---|---|---|---|---|
| Y6 |  |  |  |  |  |  |  |  |  |  |
| Y7 |  |  |  |  |  |  |  |  |  |  |
| Y8 |  |  |  |  |  |  |  |  |  |  |
| Y9 |  |  |  |  |  |  |  |  | D | D |
| Y10 |  |  |  |  |  |  |  |  |  |  |
| Y11 |  |  |  |  |  |  |  |  |  |  |
| Y12 |  |  |  |  |  |  |  |  |  |  |
| Y13 |  |  |  |  |  |  |  |  |  |  |
| Y14 | D |  |  |  | D |  |  |  |  | D |
| Y15 | D |  |  |  | D |  |  |  |  | D |
| Y16 |  |  |  |  |  |  |  |  |  |  |
| Y17 |  |  |  |  |  |  |  |  |  |  |
| Y18 |  |  |  |  |  |  |  |  | D | D |
| Y19 |  |  |  |  |  |  |  |  |  |  |
| Y20 |  |  |  |  |  |  |  |  |  |  |
| R1 |  |  |  |  |  |  |  | $CD_3$ |  | $CD_3$ |
| R2 |  |  |  | $CD_3$ | $CD_3$ |  | $CD_3$ |  |  | $CD_3$ |
| R3 |  |  |  | $CD_3$ | $CD_3$ |  | $CD_3$ |  |  | $CD_3$ |
| W1 |  |  | D |  |  |  |  |  |  | D |
| W2 |  |  | D |  |  |  |  |  |  |  |
| W3 |  | D | D |  |  |  |  |  |  | D |
| W4 |  | D | D |  |  |  |  |  |  | D |
| D Min | 2 | 2 | 4 | 6 | 8 | 1 | 7 | 3 | 2 | 18 |

TABLE 2

|  | EE90 | EE91 | EE92 | EE93 | EE94 | EE95 | EE96 | EE97 | EE98 | EE99 |
|---|---|---|---|---|---|---|---|---|---|---|
| Y1 |  |  |  |  |  |  |  |  |  |  |
| Y2 |  |  |  |  |  |  | D | D |  |  |
| Y3 |  |  |  |  |  |  |  |  |  |  |
| Y4 |  |  |  |  |  |  |  |  |  |  |
| Y5 |  |  |  |  |  |  |  |  |  |  |
| Y6 |  |  |  |  |  |  |  |  |  |  |
| Y7 |  |  |  |  |  |  |  |  |  |  |
| Y8 |  |  |  |  |  |  |  |  |  |  |
| Y9 |  |  |  |  |  |  |  |  |  | D |
| Y10 |  |  |  |  |  |  |  |  |  |  |
| Y11 |  |  |  |  |  |  |  |  |  |  |
| Y12 |  |  |  |  |  |  |  |  |  |  |
| Y13 |  |  |  |  |  |  |  |  |  |  |
| Y14 | D | D | D | D | D | D | D | D | D | D |
| Y15 | D | D | D | D | D | D | D | D | D | D |
| Y16 |  |  |  |  |  |  |  |  |  |  |
| Y17 |  |  |  |  |  |  |  |  |  |  |
| Y18 |  |  |  |  |  |  |  |  |  | D |
| Y19 |  |  |  |  |  |  |  |  |  |  |
| Y20 |  |  |  |  |  |  |  |  |  |  |
| R1 | $CD_3$ | $CD_3$ | $CD_3$ | $CD_3$ | $CD_3$ | $CD_3$ | $CD_3$ | $CD_3$ | $CD_3$ | $CD_3$ |
| R2 | $CD_3$ | $CD_3$ | $CD_3$ | $CD_3$ | $CD_3$ | $CD_3$ | $CD_3$ | $CD_3$ | $CD_3$ | $CD_3$ |
| R3 | $CD_3$ | $CD_3$ | $CD_3$ | $CD_3$ | $CD_3$ | $CD_3$ | $CD_3$ | $CD_3$ | $CD_3$ | $CD_3$ |
| W1 |  |  |  | D |  |  |  |  |  |  |
| W2 |  |  |  | D |  |  |  |  |  |  |
| W3 |  |  | D | D |  |  |  |  |  |  |
| W4 |  |  | D | D |  |  |  |  |  |  |
| D Min | 11 | 11 | 13 | 15 | 11 | 11 | 12 | 12 | 11 | 13 |

TABLE 3

|  | EE100 | EE101 | EE102 | EE103 | EE104 | EE105 | EE106 |
|---|---|---|---|---|---|---|---|
| Y1 |  |  |  | D |  | D | D |
| Y2 | D |  |  | D |  | D | D |
| Y3 |  |  |  | D |  |  | D |
| Y4 |  |  |  |  | D | D | D |
| Y5 |  |  |  |  | D | D | D |
| Y6 |  |  |  |  | D | D | D |
| Y7 |  |  |  |  |  |  |  |
| Y8 |  |  | D | D | D |  | D |
| Y9 | D |  |  | D | D |  | D |
| Y10 |  | D |  |  |  | D | D |
| Y11 |  | D |  |  |  | D | D |
| Y12 |  |  |  |  |  | D | D |
| Y13 |  |  |  |  |  | D | D |
| Y14 | D | D | D | D | D | D | D |
| Y15 | D | D | D | D | D | D | D |
| Y16 |  | D |  |  |  | D | D |

TABLE 3-continued

| | EE100 | EE101 | EE102 | EE103 | EE104 | EE105 | EE106 |
|---|---|---|---|---|---|---|---|
| Y17 | | D | | | | D | D |
| Y18 | D | | D | D | D | | D |
| Y19 | | | D | D | D | | D |
| Y20 | | | | | | | |
| R1 | $CD_3$ | $CD_3$ | $CD_3$ | $CD_3$ | $CD_3$ | $CD_3$ | $CD_3$ |
| R2 | $CD_3$ | $CD_3$ | $CD_3$ | $CD_3$ | $CD_3$ | $CD_3$ | $CD_3$ |
| R3 | $CD_3$ | $CD_3$ | $CD_3$ | $CD_3$ | $CD_3$ | $CD_3$ | $CD_3$ |
| W1 | D | D | | | D | | D |
| W2 | D | D | | | D | | D |
| W3 | D | D | | | D | | D |
| W4 | D | D | | | D | | D |
| D Min | 18 | 19 | 15 | 18 | 22 | 23 | 31 |

It has further been discovered by the inventor that as certain locants are protected from biological processing (i.e. catabolism or degradation), other sites on the deuterated elacridar molecule become secondary (and tertiary, etc) targets for catabolism. Accordingly, it becomes valuable to deuterated additional sites to protect deuterated elacridar from degradation and increase the half-life.

Considering analogs EE80-EE106 (e.g. the analogs shown in Tables 1-3), where a locant is undesignated (i.e. H or D), there is value in deuterating that undesignated site. Hence, analogs EE80-EE106 (as well as EE1-EE21) are meant to represent the species set forth (where only the designated locants are deuterated), but also a genus of compounds where additional locants are deuterated.

Taken together, embodiments of the present invention include Formula 1 with at least 5 or 10 or 15 or 20 deuterium atoms.

Deuteration Designation and Enrichment and Chemical Nomenclature

Unless otherwise stated, when a position is designated specifically as "D" or "deuterium", the position is understood to have deuterium at an abundance that is at least 3000 times greater than the natural abundance of deuterium, which is 0.015% (i.e., at least 45% incorporation of deuterium).

Instant analogs taught herein will inherently contain small amounts of isotopologues (e.g. having isotopes present at their natural isotopic abundance at locants other than those taught as substituted herein).

In other embodiments, a compound of this invention has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

In the analogs of this invention, any atom not specifically designated as a particular isotope is meant to represent any stable isotope of that atom. Unless otherwise stated, when a position is designated specifically as "H" or "hydrogen", the position is understood to have hydrogen at its natural abundance isotopic composition.

Compositions of the invention can optionally be a collection of molecules having an identical chemical structure, except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this invention will depend upon a number of factors including the isotopic purity of deuterated reagents used to make the compound and the efficiency of incorporation of deuterium in the various synthesis steps used to prepare the compound. However, as set forth above, the relative amount of such isotopologues in toto will be less than 55% of the compound. In other embodiments, the relative amount of such isotopologues ire toto will be less than 50%, less than 47.5%, less than 40%, less than 32.5%, less than 25%, less than 17.5%, less than 10%, less than 5%, less than 3%, less than 1%, or less than 0.5% of the compound.

Unless otherwise indicated, when a disclosed compound is named or depicted by a structure without specifying the stereochemistry and has one or more chiral centers, it is understood to represent all possible stereoisomers of the compound.

The analogs of the present invention may contain an asymmetric carbon atom, for example, as the result of deuterium substitution or otherwise. As such, analogs of this invention can exist as either individual enantiomers, or mixtures of the two enantiomers. Accordingly, a compound of the present invention may exist as either a racemic mixture or a scalemic mixture, or as individual respective stereoisomers that are substantially free from another possible stereoisomer. The term "substantially free of other stereoisomers" as used herein means less than 25% of other stereoisomers, preferably less than 10% of other stereoisomers, more preferably less than 5% of other stereoisomers and most preferably less than 2% of other stereoisomers are present. Methods of obtaining or synthesizing an individual enantiomer for a given compound are known in the art and may be applied as practicable to final analogs or to starting material or intermediates.

Elacridar Synthesis

Elacridar can be synthesized as described in U.S. Pat. No. 6,248,891. The skilled artisan will now readily recognize that the deuterated analogs of the present invention can be made by starting with starting compounds deuterated at the appropriate position.

Another useful method for synthesis of the instant analogs is to generally follow the methods of Dörner et al. (J Med Chem. 2009 Oct. 8; 52(19): 6073-6082) wherein reactants are synthesized with the appropriate deuterated substitution.

Another useful method of synthesis is described by Bernd et al. ("Synthesis and Small-Animal Positron Emission Tomography Evaluation of [11C]-Elacridar as a Radiotracer to Assess the Distribution of P-Glycoprotein at the Blood-Brain Barrier." Journal of medicinal chemistry 52.19 (2009): 6073-6082. PMC. Web. 6 Mar. 2018).

Figures 2, 2A:
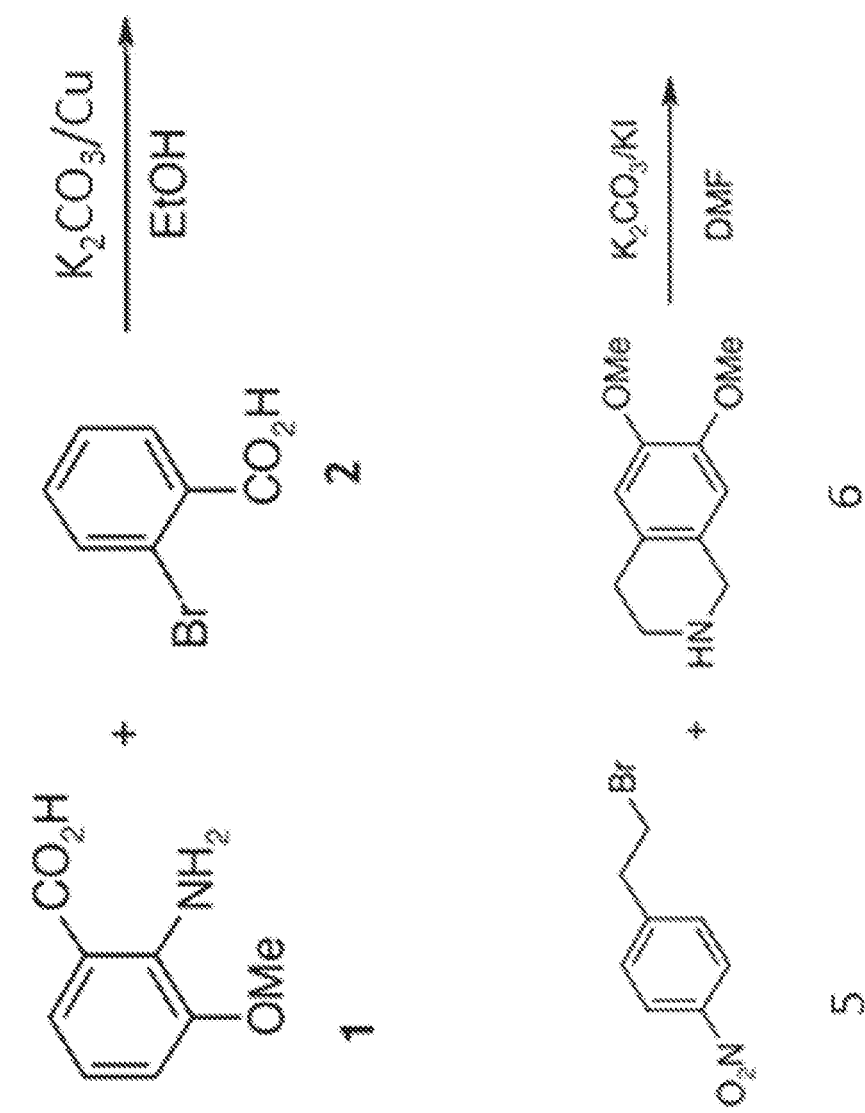
FIG. 2 shows a representative method of elacridar synthesis.
Figure 2B:
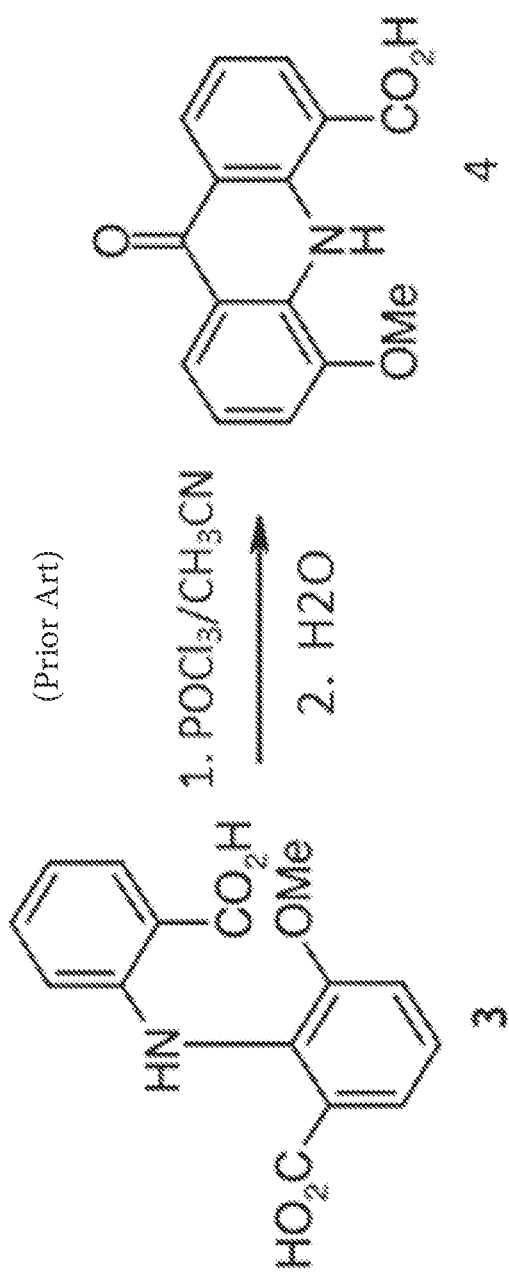
Figure 2B:
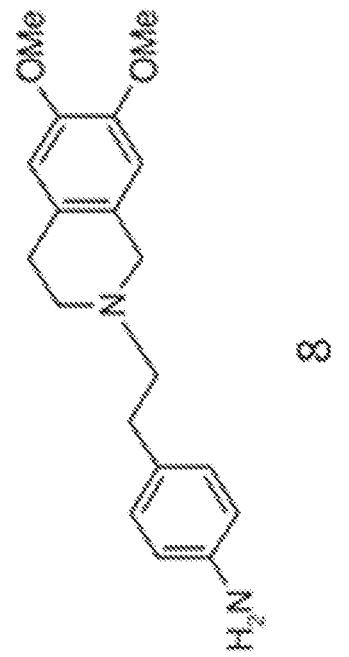
Figure 2B:
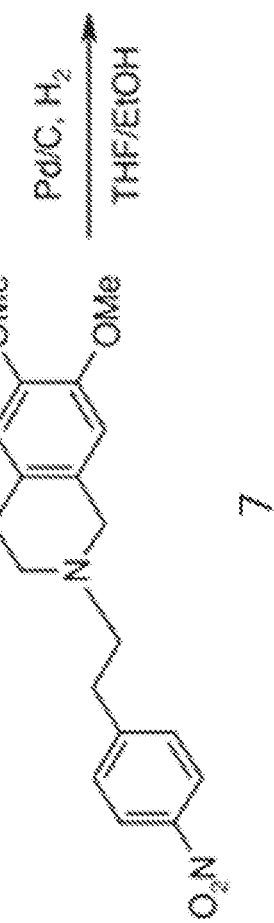
Figure 2C:
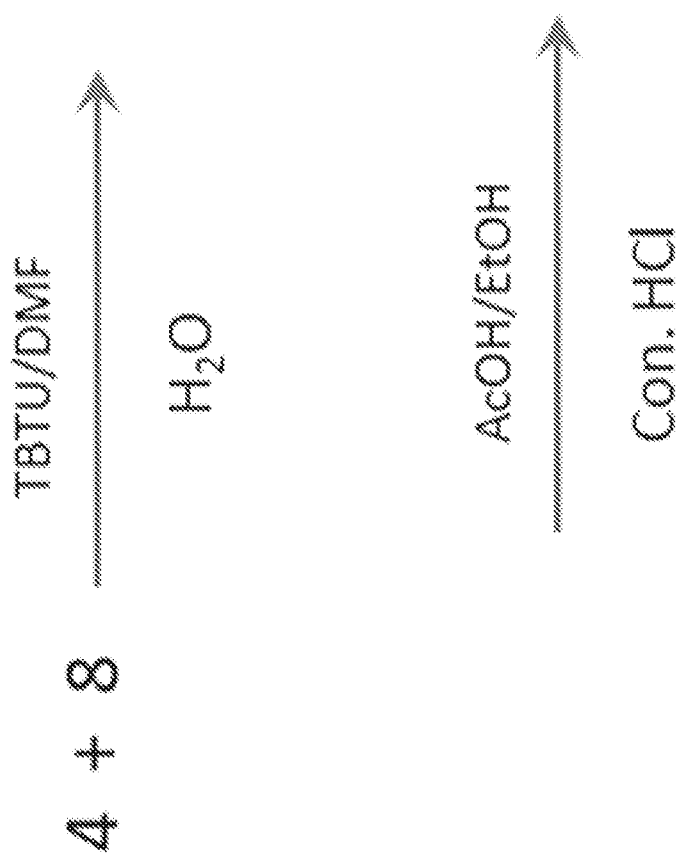
Figure 2D:
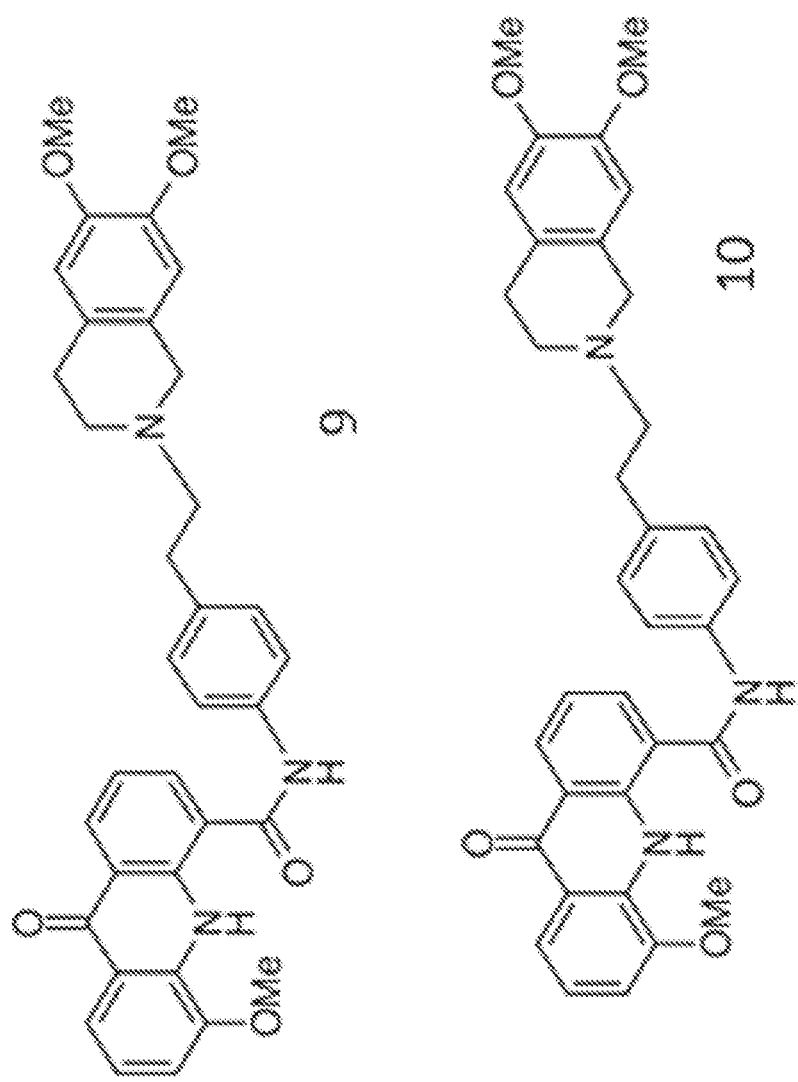
Figure 3:
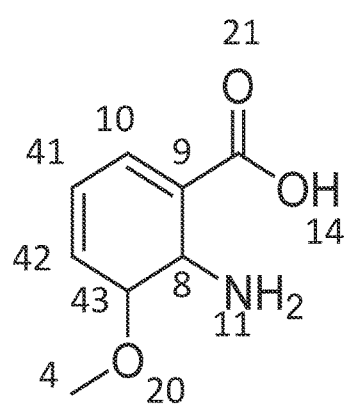
FIG. 3 shows reactant compounds for synthesis of elacridar and elacridar analogs. Locant numbers reference the final elacridar product shown in FIG. 1.
Figure 3:
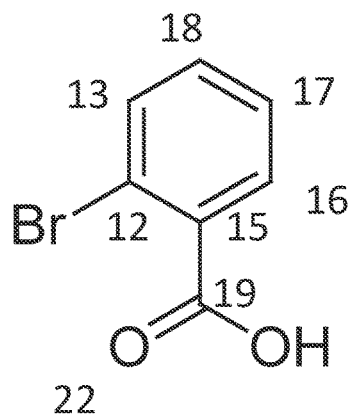
Figure 3:
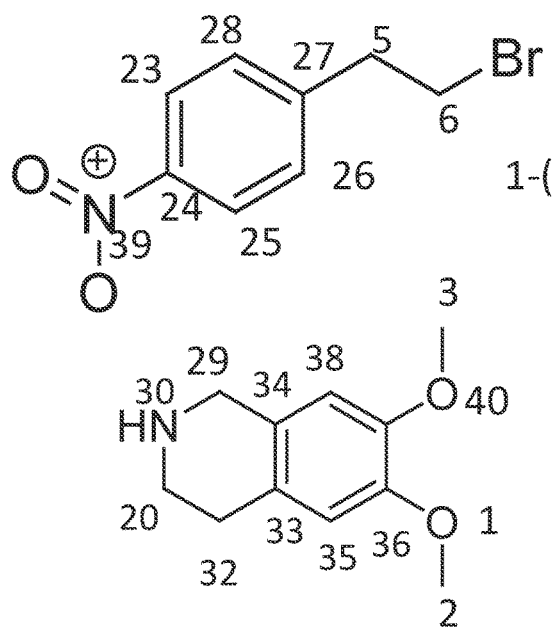

Another useful method for synthesis of the instant analogs is to generally follow the methods shown in FIG. 2. The reactants (e.g. Compounds 1, 2, 5, and 6) shown in FIG. 3 have locants numbered according to those in the final elacridar analog as shown in FIG. 1. This method is described in further detail by way of example in Example 1. Using this method, any of the elacridar analogs taught herein can be synthesized by selection of Compounds 1, 2, 5, and 6 which are deuterated appropriately. To aid in the selection of the appropriately deuterated reactants, the atoms in the reactant are numbered according to the locant numbers in elacridar (showing their location in the finished synthetic product).

Deuterium can also be incorporated to various positions, selectively or non-selectively through a proton-deuterium exchange method known in the art.

Pharmaceutical Salts

Analogs and compositions of the present invention can be prepared as pharmaceutically acceptable salts.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

The pharmaceutically acceptable salt may also be a salt of a compound of the present invention and a base. Exemplary bases include, but are not limited to, hydroxide of alkali metals including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methylamine, N-ethylamine; diethylamine; triethylamine; mono-, bis-, or tris-(2-OH—(C1-C6)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like.

Compositions, Dosage Forms and Carriers

The invention also provides pharmaceutical compositions comprising an effective amount of a compound (e.g. instant analog) of the invention and a pharmaceutically acceptable carrier. The carrier(s) are also acceptable in the sense of being compatible with the other ingredients of the formulation.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. If required, the solubility and bioavailability of the analogs of the present invention in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informs Healthcare, 2007; and "Role of Lipid Excipients in Modifying Oral and Parenteral Drug Delivery: Basic Principles and Biological Examples," Kishor M. Wasan, ed. Wiley-Interscience, 2006.

Optionally, instant compositions are in a solid or liquid form. For example, solid forms include tablets or particle-containing capsules formulated for oral administration. As another example, liquid forms include suspensions or emulsions, e.g. comprising emulsifiers or surfactants such as polysorbates or hydroxypropylmethylcellulose (Sane R, Agarwal S, Elmquist W F. Brain Distribution and Bioavailability of Elacridar after Different Routes of Administration in the Mouse. Drug Metabolism and Disposition. 2012; 40(8):1612-1619. doi:10.1124/dmd.112.045930).

Optionally, an instant composition comprises about 10 mg to about 20000 mg of an elacridar analog, e.g., about 25 mg to about 1000 mg. Other contemplated compositions are those that provide dosing as taught herein.

Optionally, an instant composition is provided in a container. For example, the container can be a sealed container, a syringe (e.g, configured for IV administration), an IV bag (e.g. mixed with a chemotherapeutic agent), a pharmacy vial configured for pills (e.g. having a child-proof lid), or a pharmacy vial configured for liquid formulation (e.g. having a sealed lid configured for puncture by a syringe).

Optionally, an instant composition is a liquid composition provided in a container other than an assay type container (e.g. other than an NMR tube or cuvette).

In one embodiment, an instant composition comprises an elacridar analog and a second therapeutic, e.g. any second therapeutic taught herein for co-administration with the elacridar analog.

In one embodiment, an instant composition is configured for any route of administration taught herein.

Routes of administration

The skilled artisan, with the teaching herein, will readily recognize the routes of administration of analogs and compositions of the present invention.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the elacridar analog is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington: The Science and Practice of Pharmacy, Lippincott Williams & Wilkins, Baltimore, Md. (20th ed. 2000).

In certain embodiments, the compound is administered orally. Compositions of the present invention suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, may also be added. For oral administration in a capsule form, useful diluents include lactose and dried cornstarch, When aqueous suspensions are administered orally, the active ingredient is optionally combined with emulsifying and suspending agents. If desired, certain sweetening and/or flavoring and/or coloring agents may be added.

Compositions suitable for oral administration include lozenges comprising the ingredients in a flavored base, usually sucrose and acacia or tragacanth; and pastilles comprising the active ingredient in an inert base such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringers solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g.: Rabinowitz J D and Zaffaroni A C, U.S. Pat. No. 6,803,031, assigned to Alexza Molecular Delivery Corporation.

Topical administration of the pharmaceutical compositions of this invention is especially useful when the desired treatment involves areas or organs readily accessible by topical application. For topical application topically to the skin, the pharmaceutical composition should be formulated with a suitable ointment containing the active components suspended or dissolved in a carrier. Carriers for topical administration of the analogs of this invention include, but are not limited to, mineral oil, liquid petroleum, white petroleum, propylene glycol, polyoxyethylene polyoxypropylene compound, emulsifying wax, and water, Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this invention may also be topically applied to the lower intestinal tract by rectal suppository formulation or in a suitable enema formulation. Topically-transdermal patches and iontophoretic administration are also included in this invention.

Application of an instant elacridar analog may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

Dosing

An elacridar analog can be provided in a specific dose. The dose amount depends, among other things, upon the route of administration. Using routine methodology, the skilled artisan can readily determine dosing amounts based on resultant plasma levels. With this said, dosing should a target plasma $C_{max}$ of greater than 10 ng/mL or greater than 20 ng/ml or greater than 40 ng/ml. With the instant invention, these plasma levels can now be achieved by oral administration of less than 2 gm or less than 1 gm or less than 0.5 gms of an elacridar analog.

Co-Administration

With the teaching herein, the skilled artisan will readily recognize the value of combining instant analogs and compositions with a second therapeutic agent or agents.

Pumps of the P-gp and/or BCRP type are known to diminish accumulation of (or therapeutic exposure of) certain therapeutic agents (e.g. those that are pump substrates)

in pump-protected target tissues, while exceeding tolerable exposure in non-pump-protected, non-target tissues. As non-limiting examples of such targets are brain and solid tumors. Accordingly, analogs and compositions of the present invention are useful when co-administered with one or more of such therapeutic agents.

Examples of therapeutic agents that are useful in combination with instant analogs or compositions are tyrosine kinase inhibitors such as dasatinib, gefitinib, matinib, pazopanib, sorafenib, sunitinib, erlotinib, and vandetanib, for example.

Other examples of therapeutic agents that are useful in combination with instant analogs or compositions are other anti-neoplastic agents such as crizotinib, docetaxel, doxorubicin, imidazotetrazine, ispinesib, paclitaxel, tazemetostat, temozolomide, and topotecan, for example.

Optionally, the second therapeutic agent is an antitumor drug. Examples of antitumor drugs include vinca alkaloids, anthracyclines, taxol and derivatives thereof, podophyllotoxins, mitoxantrone, actinomycin, colchicine, gram icidine D, amsacrine or any drug having cross resistance with above drugs characterized by the so-called multidrug resistance ('MDR') phenotype.

Other examples of therapeutic agents that are useful in combination with instant analogs or compositions are antiviral and anti-retroviral drugs such as abacavir, amprenavir, lamivudine, ritonavir, and zidovudine, for example.

Other examples of therapeutic agents that are useful in combination with instant analogs or compositions are opioid receptor agonists such as loperamide, morphine, and n-desmethylloperamide, for example.

In another embodiment, the instant invention provides separate dosage forms of an elacridar analog of this invention and one or more of any of the above-described second therapeutic agents or classes of therapeutic agents, wherein the elacridar analog and second therapeutic agent are associated with one another. The term "associated with one another" as used herein includes separate dosage forms are packaged together or otherwise attached to one another such that it is readily apparent that the separate dosage forms are intended to be sold and administered together (within less than 24 hours of one another, consecutively or simultaneously).

According to the present invention, one or more therapeutic agents and an elacridar analog can be co-administered with a second or third or fourth drug such that all drugs are present in the subject at the same time. For example, an elacridar analog can be administered before, after, or at the same time as the second drug.

Methods of Use

In one embodiment, the present invention provides a method comprising administering an instant elacridar analog to a subject in need thereof.

In another one embodiment, the present invention provides a method of enhancing the efficacy of a therapeutic agent comprising co-administering an instant elacridar analog and a therapeutic agent, where optionally, the therapeutic agent is a substrate for a P-gp pump or a BCRP pump.

For example, an instant elacridar analog can be used for sensitizing multidrug-resistant cancer cells to chemotherapeutic agents.

Optionally, the subject is a mammal or a human.
Optionally, the administration is oral or injection.

Optionally, the instant elacridar analog is administered in the form of a pharmaceutically acceptable composition taught herein.

Optionally, the method comprises co-administering a second therapeutic, e.g., a second therapeutic taught herein.

Superior and Unexpected Properties

There has been a long recognized, unmet need to provide a means of increasing drug accumulation in or distribution to certain pump-protected target tissues like solid tumors and sites in the central nervous system. The mechanisms which limit such accumulation or distribution are well known, i.e. there exist certain efflux pumps which naturally occur or are upregulated (e.g. especially in certain pathologies or induced by drug exposure) that pump such drugs away from the desired target. It has been discovered, according to the mind of the inventor, that instant analogs and compositions now provide remarkable superior properties over previously known pump inhibitors or previously used elacridar compounds and compositions. It is now possible to use the instant analogs and compositions in a manner that increases therapeutic agent accumulation in or distribution to the pump-protected target regions.

Due to the aforementioned unpredictability of results obtained from deuteration of active pharmaceutical ingredients, it is quite surprising that elacridar analogs of the present invention can improve the systemic exposure and pharmacodynamic profile relative to unsubstituted elacridar. The improved pharmacokinetics of deuterated analogs of elacridar can be demonstrated by any of improved in vivo half life, increased AUC and Cmax, reduced first pass metabolism in the GI tract and liver, and reduced metabolism demonstrated in vivo or in vitro (e.g. in a microsomal or supersomal assay). Deuterated analogs of elacridar can improve the pharmacodynamics of a coadministered therapeutic agent by increasing exposure of the therapeutic agent in pump-protected tissues and improving therapeutic response when compared to non-deuterated elacridar.

Accordingly, it is now possible to achieve and maintain therapeutic levels of a therapeutic agent in pump-protected tissues and, at the same time, reduce levels of the therapeutic agent in the systemic circulation and non-pump-protected tissues, which results in a decrease in toxicity and other adverse events. This is due to the ability to achieve therapeutic levels in the target tissues while administering lower doses of the therapeutic agent (that would otherwise be too toxic to be useful). To state this differently, the therapeutic window of certain therapeutic agents is non-existent. In order to obtain therapeutic levels in the target tissues, it would be necessary to administer toxic levels of the therapeutic agent. With the superior properties of the instant elacridar analogs, the therapeutic index is greatly enhanced.

In some embodiments, instant analogs can result in an increase in serum half life of 20% or more than 40% (when compared to a similar dose, administration, and composition of the unsubstituted elacridar). Similarly, the AUC of instant analogs can be increased by 20% or more than 40%. Similarly, when instant analogs and compositions are co-administered with a therapeutic drug which is a substrate for P-gp or BCRP-like pumps, the levels of such a therapeutic drug in pump-protected tissues such as the brain or in a solid tumor can be increased as much as 20% or 40% or more.

By way of example, increase in brain levels of the following compounds can be remarkably increased when co-administered with instant analogs and compositions (when compared to co-administration with a similar dose, administration, and composition of the unsubstituted elacridar): dasatinib, gefitinib, imatinib, pazopanib, sorafenib, sunitinib, and vandetanib, crizotinib, docetaxel, doxorubicin, imidazotetrazine, ispinesib, paclitaxel, tazemetostat, temozolomide, and topotecan, abacavir, amprenavir, lamivudine, ritonavir, zidovudine, loperamide, morphine, and n-desmethylloperamide.

As discussed above, it has also been discovered, according to the mind of the inventor, that certain elacridar metabolites are responsible for toxic effects of elacridar administration and that the instant analogs should be safer and exhibit less toxicities.

EXAMPLES

The following examples are intended to illustrate but not to limit the invention. Moreover, scientific discussions below of underlying mechanisms gleaned from the data are also not meant as limitations of the inventions described here.

Example 1: Synthesis of Instant Analogs and Compositions

This example demonstrates a synthetic method for making elacridar analogs, deuterium substitutions based upon the deuteration of the starting compounds. The synthesis and the analog numbers refer to FIG. 4.

Step 1

A 12 L three-neck flask was charged with compound 1 (270.5 g, 1.618 mol), compound 2 (357.8 g, 1.78 mol, 1.1 eq.), $K_2CO_3$ (447 g, 3.236 mol, 2.0 eq), Cu (20.6 g, 0.324 mol, 0.2 eq.) and ethanol (2.7 L) and the resulting mixture was heated to reflux under nitrogen for 1 hour. The reaction mixture was cooled to room temperature after the reaction progress was checked with LC-MS. Water (2.7 L) was added and the mixture was filtered through a pad of Celite. The Celite was washed with water (1.35 L) and the combined filtrate was adjusted to pH-2 by addition of concentrated HCl (~410 mL) over 15 min. The resulting suspension was stirred at 10° C. for 1.5 hours and the solid was filtered, washed with water (2.7 L) and dried at 45° C. using a vacuum oven for 2 days to give compound 3 (465 g, H 00%) as a yellow solid.

Step 2

A suspension of compound 3 (498 g, 1.734 mol) in acetonitrile (4.0 L) was heated to reflux under stirring. To the suspension was added $POCl_3$ (355.5 mL, 3.814 mol, 2.2 eq.) drop-wise over 2 h. The mixture was heated at reflux for 2.5 h and then cooled to 30° C. To the mixture was slowly added water (3.0 L) and the resultant thick slurry was heated to reflux for 1.5 h. The slurry was cooled to 10° C. and filtered. The solid was washed with water (2×1.0 L), acetonitrile (2×1.0 L) and dried using a vacuum oven overnight at 45° C. to afford compound 4 (426 g, 91.3%) as a yellow solid.

Step 3

A 12 L three-neck flask was charged with compound 5 (475 g, 2.065 mol), compound 6 (474.8 g, 2.065 mol), $K_2CO_3$ (314 g, 2.273 mol), KI (68.6g, 0.413 moL) and DMF (2.5 L) and the resulting mixture was heated to 70° C. and stirred for 2.5 hours. After LC-MS showed that the reaction was complete, the mixture was cooled to 50° C. and methanol (620 mL) was added. Then the mixture was cooled to 30° C. and water (4.75 L) was added. The resulting suspension was cooled to 10° C. and for 1 hour. The solid was filtered, washed with water (2×2.5 L) and air dried for 2 days to afford the compound 7 (630 g, 89.1%) as a yellow solid.

Step 4

To a solution of compound 7 (630 g, 1.84 mol) in THF/ethanol (8 L at 1:1) was added Pd/C (10%, 50% wet, 30 g). The mixture was stirred under an atmosphere of hydrogen (1 atm, balloon) at 15-20° C. for 4 h. The reaction mixture was filtered through a pad of Celite and the pad was washed with THF (1.0 L). The filtrate was concentrated to 3 volumes under vacuum and hexanes (4.0 L) was added. The resulting slurry was cooled to 0° C. and stirred for 1 h. The solid was filtered and washed with hexanes (2×500 mL) and air dried overnight to afford the compound 8 (522 g, 90.8%) as an off-white solid.

Step 5

A 5 L three-neck flask was charged with compound 4 (250 g, 0.929 mol, 1 eq.), compound 8 (290 g, 0.929 mol, 1 eq.) and DMF (2.5 L) and the resulting mixture was stirred at room temperature until it became a clear solution. To the solution was added TBTU (328 g, 1.021 mol, 1.1 eq.), followed by triethylamine (272 mL, 1.95 mol, 2.1 eq.) and the resulting mixture was stirred at room temperature under nitrogen overnight. The mixture was poured slowly into water (7.5 L) with stirring and the resulting suspension was stirred for 1 hour at room temperature. The solid was filtered and washed with water (2×7 L). The solid thus obtained was dried using a vacuum oven at 50° C. for two days and 509.0 g (97.3%) of compound 9 was obtained as yellow solid.

Step 6

300.0 g (0.532 mol) of compound 9 was suspended in acetic acid (1.2 L) and heated to 70° C. The resultant solution was hot filtered and heated to 70° C. again. Preheated ethanol (70° C., 3.6 L) was then added. To this solution was added concentrated HCl (66.0 mL, 0.792 mol, 1.5 eq.) dropwise over 30 min. The resulting solution was stirred at 70° C. until crystallization commenced (about 20 min). The suspension was cooled to room temperature over 3 h, filtered, washed with ethanol (2×1.8 L) and dried using a vacuum oven at 60° C. over the weekend to afford compound 10 (253.0 g, 79.2%) as a brown solid.

Example 2 Manufacture of a Deuterated Elacridar Analog EE60

Figure 4:
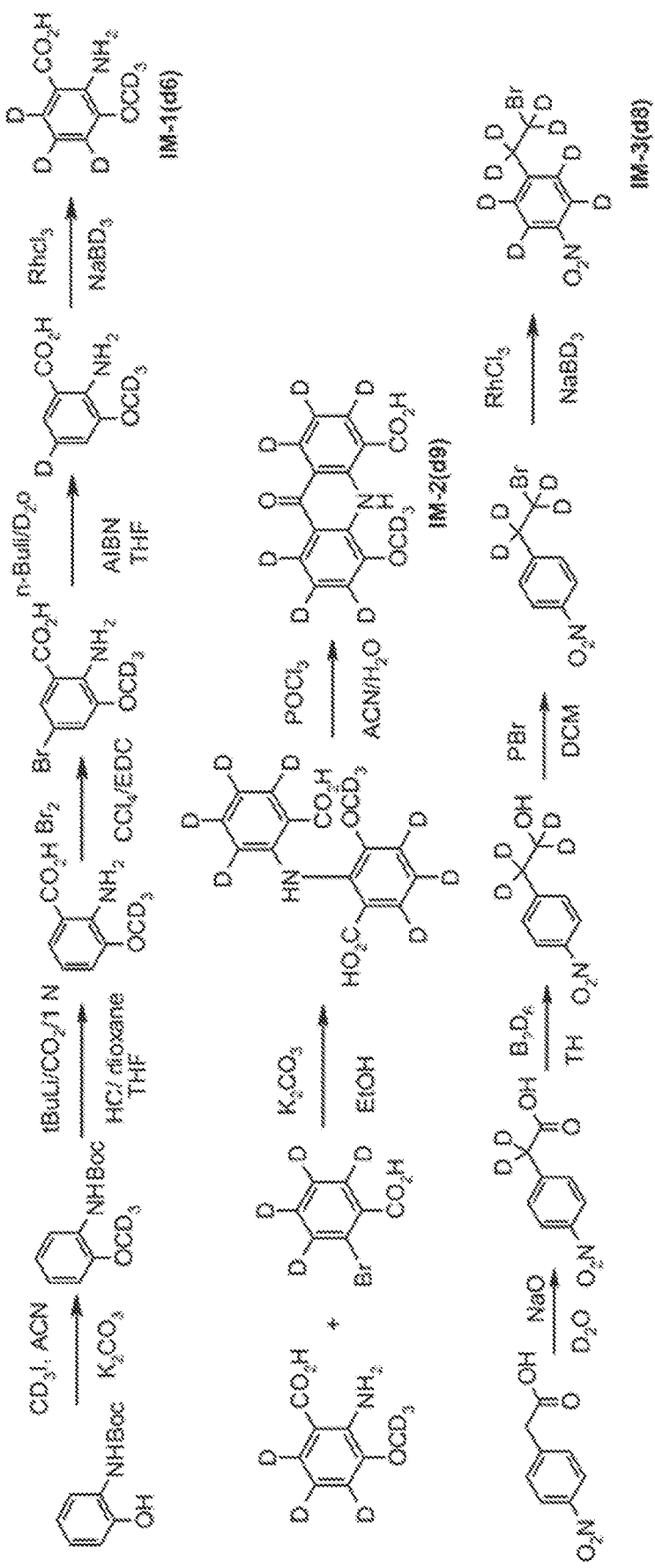
FIG. 4 shows a representative method of the first steps of synthesis of EE60.
Figure 5:
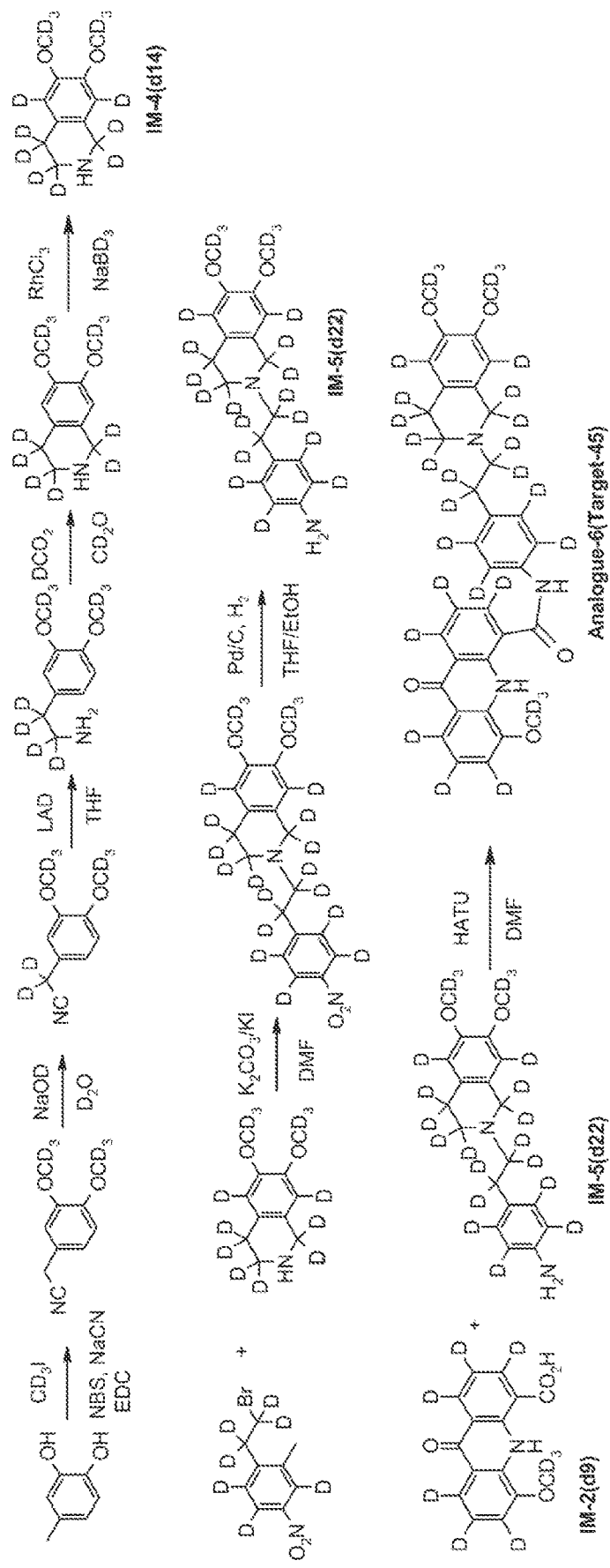
FIG. 5 shows a representative method of the last steps of synthesis of EE60

EE60 is synthesized by the procedure shown in FIG. 4 and as continued in FIG. 5.

The structure of EE60 is confirmed as follows: Samples of 5 µl are measured using an LC system comprising an UltiMate 3000 LC Systems (Dionex, Sunnyvale, Calif.) and an 2996 UV diode array detector (Waters). Samples are injected on to a 100×2 mm (ID) 3.5 µm ZORBAX Extend-018 column (Agilent, Santa Clara, Calif.). Elution is done at a flow rate of 0.4 mL/min using a 5 minute gradient from 20% to 95% B (mobile phase A was 0.1% HCOOH in water (v/v) and mobile phase B was methanol). 95% B is maintained for 1 min followed by re-equilibration at 20% B. Chromeleon (v6.8) is used for data acquisition and peak processing.

Example 3: Manufacture of a Deuterated Elacridar Analog EE59

Figure 6:
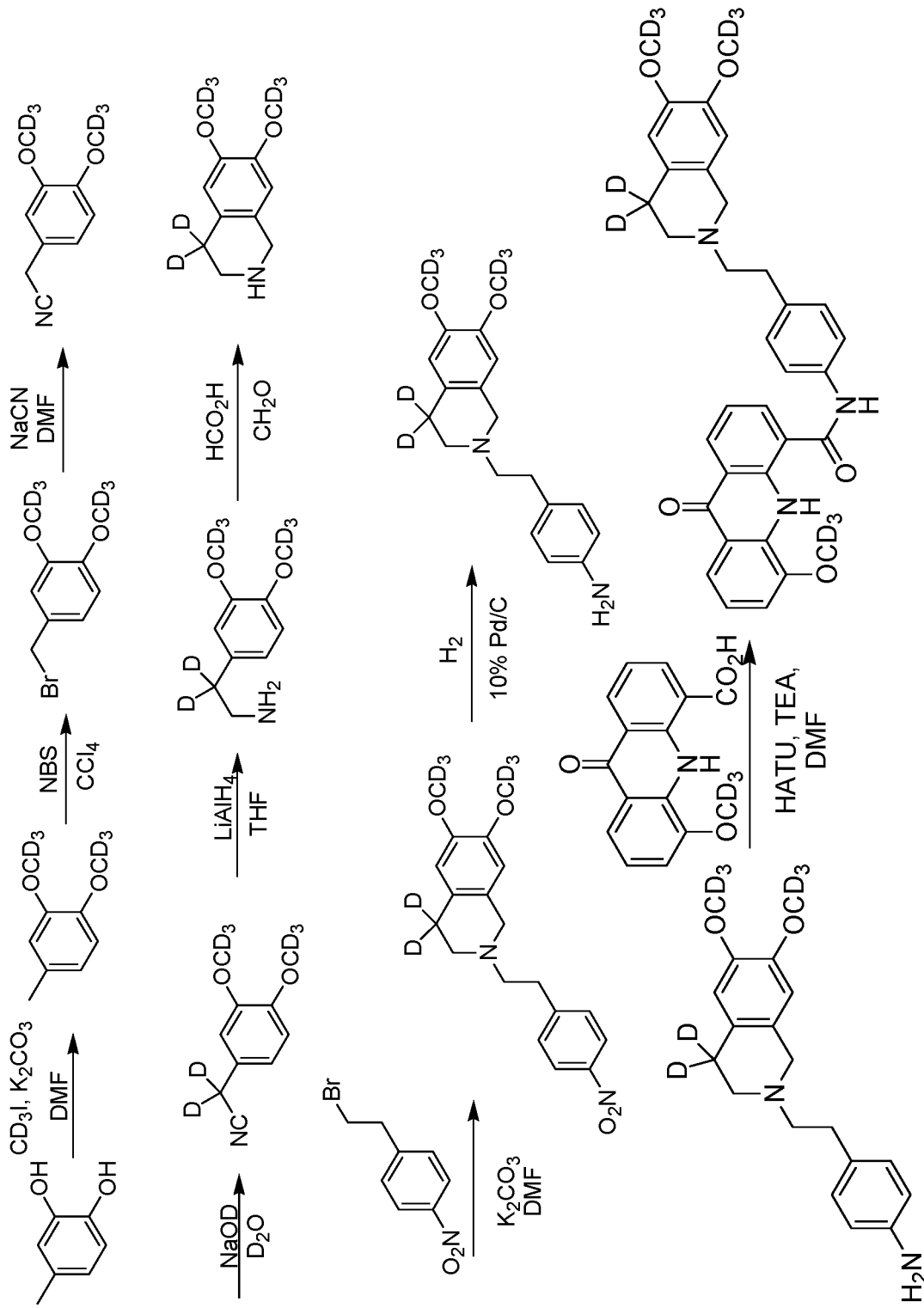
FIG. 6 shows a representative method of synthesis of EE59.
Figure 7:
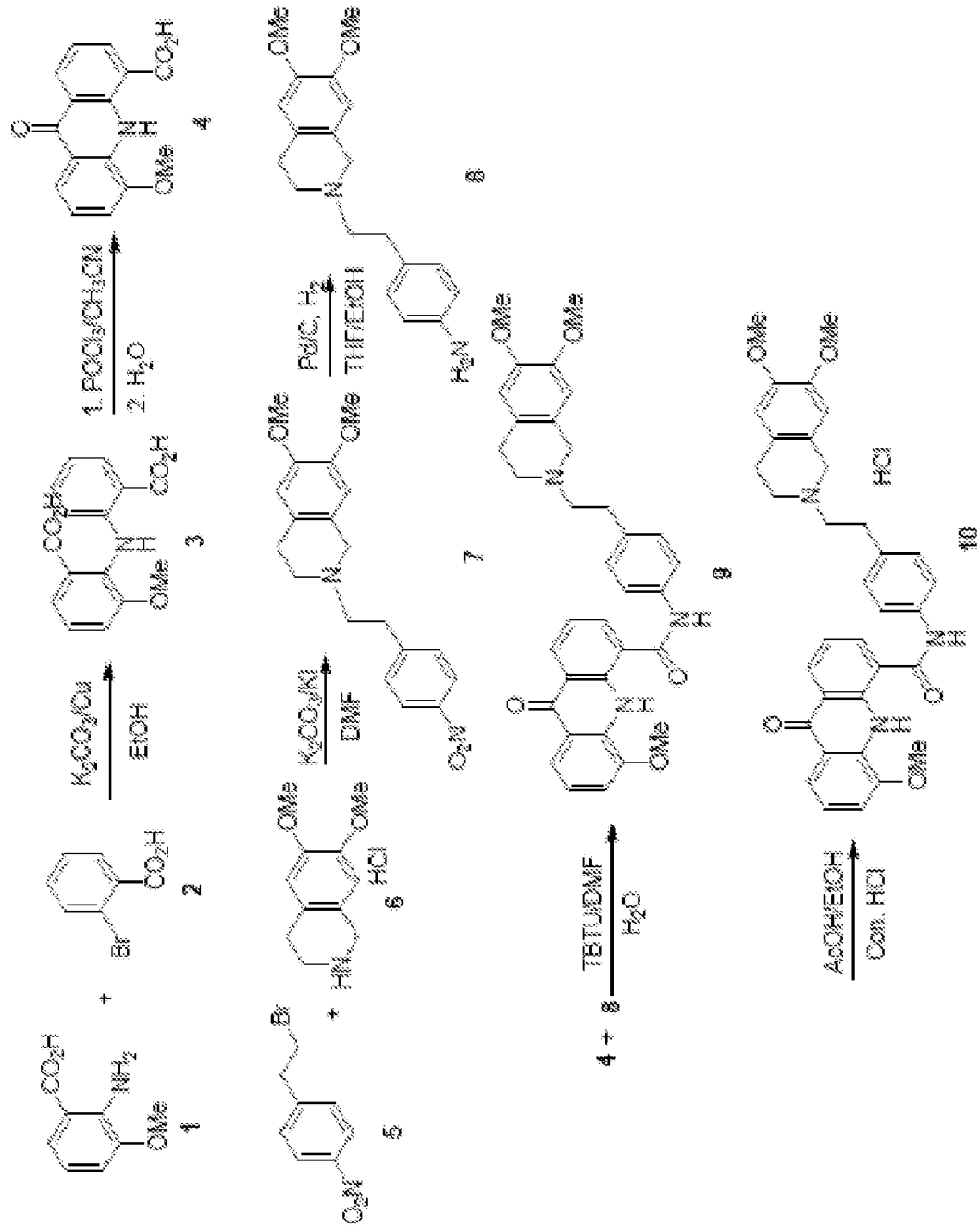
FIG. 7 is a reproduction of FIG. 2.

EE59 was synthesized by the procedure shown in FIG. 6.

The resulting yellowish brown precipitate was removed by filtration and the filter cake was dried overnight (72 mg). Analysis of the filter cake by LCMS indicated the presence of a single peak at multiple wavelengths (215 nm, 220 nm, 254 nm, 280 nm); each peak confirmed the presence of the desired product (LC retention time, 5.3 min; m/z=575 [(M+H)+]), $^1$H NMR of EE598 revealed $^1$H NMR (400 MHz, DMSO-d$_6$) δ 12.3 (s, 1H), 10.6 (s, 1H), 8.51-8.46 (m, 2H), 7.80 (d, J=8.8 Hz, 1H), 7.66 (d, J=7.6 Hz, 2H), 7.45-7.38 (m, 2H), 7.32-7.25 (m, 3H), 6.66 (d, J=6.8 Hz, 2H), 3.62 (s, 2H), 2.86 (t, J=6.8 Hz, 2H), 2.66 (m, 4H).

Example 4: Demonstration of Superior Properties of Instant Analogs and Compositions: In Vivo ADMET Pharmacologic studies are performed according to Ward K W et al (2001 *Xenobiotica* 31:783-797) and Ward and Azzarano (JPET 310:703-709, 2004). Briefly, instant analogs are administered solutions in 10% aqueous polyethylene glycol-300 (PEG-300) or 6% Cavitron with 1% dimethyl sulfoxide, or as well triturated suspensions in 0.5% aqueous HPMC containing 1% Tween 80. Blood samples are collected at various times up to 48 h after drug administration; plasma samples are prepared and at "70° C. until analysis.

Mice. Instant analogs are administered to four groups of animals by oral gavage (10 ml/kg dose volume). Three groups receive instant analogs as a suspension at 3, 30, or 300 mg/kg, and the fourth group receive instant analogs as a solution in Cavitron at 3 mg/kg. Blood sampling in mice is performed via a tail vein at 0.5, 1, 2, 4, 8, 24, and 32 h postdose.

Rats. A total of seven groups of animals receive instant analogs by oral gavage (10 ml/kg). Three groups receive instant analogs as a suspension at 3, 30, or 300 mg/kg, and a fourth and fifth group each receive instant analogs as a solution in Cavitron or PEG-300, respectively, at 3 mg/kg. A sixth and seventh group of rats with indwelling hepatic portal vein catheters receive instant analogs by oral gavage (10 ml/kg) as a suspension at 3 or 30 mg/kg, respectively. Blood sampling in rats are performed via a lateral tail vein; samples are also obtained from the hepatic portal vein catheter. Blood samples are obtained before dosing and at 5, 15, 30, and 45 min, and 1, 1.5, 2, 3, 4, 6, 8, 10, 24, and 32 h postdose.

Dogs. Dogs receive instant analogs by lavage (4 ml/kg) on three separate occasions with dosages at 3 and 30 mg/kg as a suspension and 3 mg/kg as a solution in Cavitron. Blood samples are obtained from a cephalic vein and from the hepatic portal vein catheter before dosing and at 5, 15, 30, and 45 min and 1, 1.5, 2, 3, 4, 6, 8, 10, 24, 32, and 48 h postdose.

Monkeys. Monkeys receive instant analogs by oral gavage (8 ml/kg dose volume) on three separate occasions at dosages of 3 and 30 mg/kg as a suspension and 3 mg/kg as a solution in Cavitron. Blood samples are obtained from a femoral vein via an indwelling catheter and from the hepatic portal vascular access port before dosing and at 5, 15, and 30 min and 1, 1.5, 2, 4, 6, 8, 10, 24, 32, and 48 h postdose.

Humans. Healthy volunteers receive instant analogs orally at doses ranging from 25 mg to 1000 mg. Blood samples are obtained and analyzed for analog concentrations at 0, 15 min, 30 min, 45 min, 60 min, 90 min, 120 min, 180 min, 2 hr, 4 hr, 6 hr, 8 hr, 12 hr, 24 hr, and 48 h after administration.

Analytical Methods

Instant analogs are isolated from samples by precipitation with acetonitrile and quantified by LC/MS/MS coupled with an atmospheric pressure chemical ionization interface (475° C.). Internal standards [in acetonitrile/10 mM ammonium formate, pH 3.0; 95:5 (v/v)] are added to 50 μl samples and vortexed and centrifuged for 30 min at 4000 rpm. The supernatants are injected onto the LC/MS/MS system using an HTS PAL autosampler (CTC Analytics, Zwingen, Switzerland) coupled to an Aria TX2 high-throughput liquid chromatographic system using turbulent flow technology (Cohesive Technologies, Franklin, Mass.) in focus mode. The mobile phase consists of a mixture of 0.1% formic acid in water and 0.1% formic acid in acetonitrile, The turbulent flow column is a 0.5×50-mm Cyclone P column (Cohesive Technologies) in series to a 2×20 mm, 4 μm Polar RP (Phenomenex, Torrance, Calif.) analytical column. Positive-ion multiple reaction monitoring is used for the detection of instant analogs and internal standard and the selected precursor and product ions are m/z 564 and 252, respectively. Using a (1/x) weighted linear regression analysis of the calibration curve, linear responses in analyte/internal standard peak area ratios are observed for instant analog concentrations ranging from 2 to 10,000 ng/ml.

Alternatively, useful analytical methods to demonstrate the surprising and superior properties of the instant elacridar analogs are the methods as described by Stokvis et al, J Mass Spectr 2004: 39: 1122-1130.

Pharmacokinetic Data Analysis.

Concentration versus time profiles are obtained for each analyte in each animal and noncompartmental analysis is performed using WinNonlin Professional version 3.3 (Pharsight, Mountain View, Calif.) to recover area under the curve (AUC), Cmax and other parameters. Dose-normalized AUC (DNAUC) (minutes X kilograms per liter) is determined by dividing AUC by dose (milligrams per kilogram) and multiplying by 1000. For studies for which both portal and systemic data are available, absorption and first-pass hepatic extraction is estimated as described by (Ward et al., 2001 (Dug Metab Dispos 29:82-88.).

Results

There is substantial species variability between the mouse, rat, dog, monkey, and human species. Nevertheless, according to insight in the mind of the inventor, instant analogs have one or more of the following superior properties when compared to the same dose of (unsubstituted) elacridar: (1) increased AUC; (2) increased DNAUC; (3) decreased pre-systemic clearance: (4) increased Cmax; (5) increased Tmax; (6) increased half-life and (7) increased absorption rate.

Example 5: Demonstration of Superior Properties of Instant Analogs and Compositions: In Vitro Metabolism This study is designed to predict biotransformation of elacridar in a model for hepatic metabolism and to compare it with the instant analogs. Additionally, the effect of CYP450 inhibitors such as ritonavir on the metabolic conversion is examined.

In one study, a human liver microsomal system is used; the microsomes are obtained from a commercial source (Thermo Scientific). Additionally, liver microsomes from the wildtype, Cyp3a knockout and Cyp3a KO; and CYP3A4 transgenic mice are prepared.

Bioconversion of elacridar and instant analogs at various concentrations are incubated with microsomes in a NADPH regenerating system as described by Cheng et al. (Nat Protoc 2009; 4: 1258-1261) and Hendrikx et al (Int J Cancer 2013; 132: 2439-2447).

Elacridar and instant analogs are monitored using liquid chromatography coupled Ultraviolet-photodiode array (LC-UV-PDA), fluorescence detection (FD) and LC-mass spectrometry or as described in Example 2.

The in vitro metabolic studies are performed in the absence and in the presence of inhibitors such as CYP3A4: ritonavir, ketoconazole; CYP3A4/CYP2C19: fluconazole; CYP2C19/CYP2A6: fluoxetine; CYP2C8: clopidogrel to identify indirectly the enzymes responsible for bioconversion.

Results.

The results, through insight in the mind of the inventor, will show the following: the instant analogs (for example, especially EE49-EE60) will have one or more of the following superior properties when compared to the unsubstituted elacridar parent (1) the half-life of the analogue is increased; (2) one or more minor metabolites appear upon incubation of instant elacridar analogs, but at a greatly reduced rate and abundance; and (3) certain metabolites that are present upon incubation of the elacridar samples are absent or nearly absent from the instant elacridar analog samples. The results when elacridar analogs are incubated in the presence of various CYP inhibitors suggest that the biotransformation is the result of an enzymatic process and that such process can be prevented or diminished by the deuterations taught herein.

Example 6: Demonstration of Superior Properties of Instant Analogs and Compositions: Facilitating Accumulation/Distribution of a Co-Administered Therapeutic Agent to Pump-protected Target Sites This example uses co-administration of instant analogs (in comparison to unsubstituted elacridar) with erlotinib, a dual substrate for P-gp and BCRP. It is well known that the presence of P-gp and BCRP at the blood brain barrier greatly limits the erlotinib bioavailability in the brain. Instant elacridar analogs and unsubstituted elacridar are individually administered with erlotinib in 20 mg/kg p.o. dose to wild type rats. The rats are either pretreated with either (1) instant analogs or (2) unsubstituted elacridar at various doses (e.g. 10 mg/kg). The plasma and brain concentrations of erlotinib are measured at various times (e.g. at 30 min, 1, 2, 4, 8, and 12 h after dose).

By insight in the mind of the inventor, instant analogs (for example, especially EE49-EE60 and EE80-EE106) provide remarkable increase in brain concentration of erlotinib when compared to similar administrations of unsubstituted elacridar. Moreover, toxicity is also reduced iwith the instant analogs when compared to unsubstituted elacridar.

I claim:

1. An analog with a structure represented by formula 1

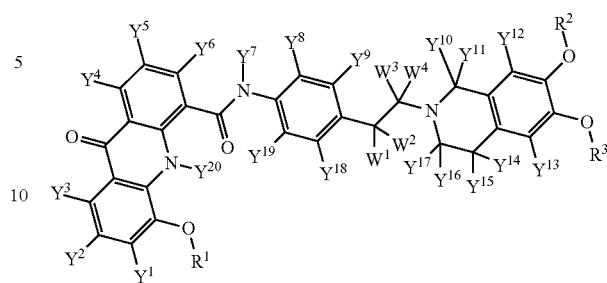

Formula 1 or a pharmaceutically acceptable salt thereof, comprising at least one deuterium atom wherein:
  each Y and each W is independently selected from hydrogen or deuterium;
  each R is independently selected from $CH_3$, $CH_2D_1$, $CH_1D_2$, and $CD_3$ with the proviso that when each Y is H and when each R is $CH_3$, then at least one W is H; and the analog further comprises a structural feature and exhibits greater metabolic stability compared to a compound of Formula I in which each Y and each W is hydrogen and each R is $CH_3$, wherein the structural feature is selected from:
  (a) Y14 and Y15 each consist of deuterium and optionally wherein each of the remaining Ys, and each of the Ws and Rs do not comprise a deuterium;
  (b) R2 and R3 each consist of CD3 and optionally wherein each of the Ys and Ws, and the remaining R, do not comprise a deuterium;
  (c) R2 and R3 each consist of CD3 and wherein Y14 and Y15 each consist of deuterium and optionally wherein each of the remaining Ys, each of the Ws, and the remaining R do not comprise a deuterium;
  (d) Y2 is deuterium and optionally wherein each of the remaining Ys, and each of the Ws and Rs do not comprise a deuterium;
  (e) Y2 is deuterium and R2 and R3 each consist of CD3 and optionally wherein each of the remaining Ys, each of the Ws, and the remaining R do not comprise a deuterium;
  (f) R1 is CD3 and Y14 and Y15 each consist of deuterium and optionally wherein each of the remaining Ys, each of the Ws, and each of the remaining Rs do not comprise a deuterium;
  (g) Y9 and Y18 each consist of deuterium and optionally wherein each of the remaining Ys and each of the Ws and Rs do not comprise a deuterium;
  (h) Y2, Y9, Y18, and W1-W4 each consist of deuterium and R1-R3 each consist of CD3 and optionally wherein each of the remaining Ys do not comprise a deuterium; or
  (i) R1, R2 and R3 each consist of CD3 and Y14 and Y15 each consist of deuterium and wherein each of the remaining Ys and each of the Ws do not comprise a deuterium.

2. A pharmaceutical composition comprising the analog of claim 1 wherein the analog has an isotopic purity of greater than 70%.

3. A pharmaceutical composition comprising the analog of claim 1 and a pharmaceutically acceptable carrier.

4. A pharmaceutical composition comprising the analog of claim 1 and one or more therapeutic agents.

5. A method comprising administering the pharmaceutical composition of claim 3 to a subject having a condition benefited by a therapeutic agent that is a substrate of a P-gp pump or a BCRP pump.

6. The method of claim 5 further comprising administering of a therapeutic amount of the therapeutic agent.

7. The pharmaceutical composition of claim 4 wherein the one or more therapeutic agents comprise one or more of a tyrosine kinase inhibitor, an anti-neoplastic agent, an anti-tumor agent, an antiviral agent, an anti-retroviral drug, and an opioid receptor agonist.

8. The pharmaceutical composition of claim 7 wherein the one or more therapeutic agents comprise one or more of topotecan, dasatinib, gefitinib, imatinib, pazopanib, sorafenib, sunitinib, vandetanib, erlotinib, crizotinib, docetaxel, doxorubicin, imidazotetrazine, ispinesib, paclitaxel, tazemetostat, temozolomide, topotecan, vinca alkaloid, anthracyclines, paclitaxel derivatives, podophyllotoxins, mitoxantrone, actinomycin, colchicine, gramicidine D, amsacrine, abacavir, amprenavir, lamivudine, ritonavir, zidovudine, loperamide, morphine, n-desmethylloperamide, and pazopanib.

9. The analog of claim 1, wherein Y14 and Y15 each consist of deuterium.

10. The analog of claim 1, wherein R2 and R3 each consist of CD3.

11. The analog of claim 1, wherein R2 and R3 each consist of CD3 and wherein Y14 and Y15 each consist of deuterium.

12. The analog of claim 11, wherein R1 consists of CD3.

13. The analog of claim 12, wherein each of the Ws and the remaining Ys do not comprise a deuterium.

14. A pharmaceutical composition comprising an amount of the analog of claim 12, wherein the pharmaceutical composition contains a total amount of isotopologues of the analog, wherein the isotopologues have hydrogen at one or more of R1-R3, Y14, and Y15, and wherein the total amount of the isotopologues is less than 25% relative to the amount of the analog.

15. A method comprising administering the analog of claim 1 to a subject.

16. A method comprising administering the analog of claim 9 to a subject.

17. A method comprising administering the analog of claim 10 to a subject.

18. A method comprising administering the analog of claim 11 to a subject.

19. A method comprising administering the analog of claim 11 to a subject.

20. A method comprising administering the analog of claim 12 to a subject.

* * * * *